(12) United States Patent
Accetta

(10) Patent No.: US 10,145,789 B2
(45) Date of Patent: Dec. 4, 2018

(54) IMMERSION REFRACTOMETER

(71) Applicant: Joseph Samuel Accetta, Corrales, NM (US)

(72) Inventor: Joseph Samuel Accetta, Corrales, NM (US)

(73) Assignee: Joseph Samuel Accetta, Albuquerque, NM (US)

( * ) Notice: Subject to any disclaimer, the term of this patent is extended or adjusted under 35 U.S.C. 154(b) by 74 days.

(21) Appl. No.: 15/218,494

(22) Filed: Jul. 25, 2016

(65) Prior Publication Data

US 2018/0024052 A1    Jan. 25, 2018

(51) Int. Cl.
*G01N 21/41*    (2006.01)

(52) U.S. Cl.
CPC .......... *G01N 21/41* (2013.01); *G01N 21/4133* (2013.01)

(58) Field of Classification Search
None
See application file for complete search history.

(56) References Cited

U.S. PATENT DOCUMENTS

| | | | | |
|---|---|---|---|---|
| 2,569,127 A * | 9/1951 | Eltenton | ............... | G01N 21/431 137/93 |
| 3,311,014 A * | 3/1967 | Witt | ...................... | G01N 21/431 250/227.25 |
| 3,977,790 A * | 8/1976 | Schweizer | ........... | G01N 21/431 356/136 |
| 4,287,427 A * | 9/1981 | Scifres | ................ | G01N 21/431 250/577 |
| 4,306,805 A * | 12/1981 | Arrington | ............ | G01N 21/431 356/133 |
| 5,026,139 A * | 6/1991 | Klainer | ................ | G01N 21/431 356/128 |
| 5,048,952 A * | 9/1991 | Miyata | ................. | G01N 21/431 123/613 |
| 5,055,699 A * | 10/1991 | Konig | .................. | G01N 21/431 250/577 |
| 5,110,205 A * | 5/1992 | Suzuki | ............... | G01N 33/2852 356/135 |
| 5,311,274 A | 5/1994 | Cole | | |
| 5,949,219 A * | 9/1999 | Weiss | ..................... | G01N 21/31 320/136 |
| 6,356,675 B1 | 3/2002 | Weiss | | |
| 6,480,638 B1 | 11/2002 | Adkins et al. | | |
| 6,538,727 B2 * | 3/2003 | Nicholas | ............. | G01N 21/431 356/133 |
| 7,283,220 B2 | 10/2007 | Huang et al. | | |
| 7,295,295 B2 | 11/2007 | Lambert et al. | | |
| 7,541,573 B2 | 6/2009 | Emmerson et al. | | |

(Continued)

*Primary Examiner* — Charlie Y Peng
(74) *Attorney, Agent, or Firm* — The Grafe Law Office

(57) ABSTRACT

A device for measuring the absolute value of the refractive index of a liquid by immersion uses the optical properties of a cylindrical waveguide with a solid core and normal angle of incidence of the light source. The device consists of a transparent tube forming the enclosure of the waveguide, impervious to the surrounding liquid and partially filled with a transparent solid or liquid material of appropriate index of refraction, a fiber optic means of inputting light via a LED or laser and fiber optic means of coupling emerging light to a photodetector. The emerging light intensity is a function of the index of refraction of the surrounding liquid.

14 Claims, 7 Drawing Sheets

(56) References Cited

U.S. PATENT DOCUMENTS

| | | |
|---|---|---|
| 7,947,945 B2 | 5/2011 | Bookbinder et al. |
| 9,046,494 B2 | 6/2015 | Song et al. |
| 2003/0112443 A1* | 6/2003 | Hjelme .................. G01N 21/45 356/480 |
| 2004/0047535 A1 | 3/2004 | Ukrainczyk |

* cited by examiner

IMMERSION REFRACTOMETER

BACKGROUND OF THE INVENTION

The field of this invention is the measurement of the index of refraction of liquids. These instruments, known as refractometers, are of 4 main types: traditional handheld refractometers, digital handheld refractometers, laboratory or Abbe refractometers, and inline process refractometers. Although refractometers are typically used for measuring the refractive index of liquids, they can be used to measure gases and solids for example the Rayleigh Refractometer used (typically) for measuring the refractive indices of gases. Refractometers may be calibrated in other engineering units such as specific gravity for example because of the predictable relationship between refractive index and specific gravity in many liquid solutions.

Traditional hand held refractometers rely on the critical angle principle. When the critical angle of incident light on an interface is exceeded total reflection occurs. The refracted angle of incident light is a function of the angle of incidence and the index of refraction of the liquid to be measured and related through Snell's Law.

Handheld refractometers use a small quantity of liquid that is placed between a prism and a small cover plate. Light traveling through the sample is either passed through to the reticle or totally internally reflected. The net effect is that a shadow line forms between the illuminated area and the dark area. It is where this shadow line crosses the scale that a reading is taken. The prism projects a shadow line onto a small glass reticle inside the instrument. The reticle is then viewed by the user through a magnifying eyepiece. Certain digital versions of this technique rely on an array of photodetectors to measure the position of the shadow line.

The necessity of placing a small quantity of liquid inside the instrument is an impediment to convenient, rapid and safe measurement of liquids that in some cases may be hazardous such as acids. It is clear that an instrument that can make the refractive index measurement by direct immersion in the container and is impervious to corrosive fluids would be both a considerable convenience and a safety measure and thus a need exists for such a device.

In the Abbe' refractometer the liquid sample is sandwiched into a thin layer between an illuminating prism and a refracting prism. Abbe' refractometers are most easily used for measuring the index of solids.

Process control refractometers are designed to monitor the refractive index under continuous flow conditions such as oil refining and various chemical processes. These refractometers rely on conventional fiber optics using the liquid as the cladding as described above and suffer from a number of shortcomings including susceptibility to corrosive liquids.

BRIEF SUMMARY OF THE INVENTION

A device for measuring the absolute value of the refractive index of a liquid by immersion uses the optical properties of a cylindrical waveguide with a solid core and normal angle of incidence of the light source. The principle of operation can be described by using analogy to fiber optic light transmission whereby the relationship between the indices of refraction of the core ($n_{co}$) and cladding ($n_{cl}$) of the fiber for efficient propagation through the fiber is given as:

$$(n_{co}^2 - n_{cl}^2)^{1/2} > 1 \qquad (1)$$

The device is essentially a cylindrical non-conducting waveguide consisting of a transparent tube that transmits light along its axis by the process of total internal reflection similar to the mechanism at work in conventional multimode fiber optics. The surrounding liquid provides an external loss mechanism depending on its refractive index. As such the device is not strongly affected by particulate matter that may be present.

In the foregoing embodiment of the device, the liquid to be measured becomes the analog to the cladding of the fiber and the solid core of the waveguide is the analog to the core of the fiber. The index of the core is chosen for compatibility with the liquid to be measured to ensure efficient propagation. The configuration of the device is well suited to measure the refractive index of the surrounding liquid by immersion of the active region of the core. The active region on the core is surrounded by a transparent and impervious substance such as glass or quartz whose refractive index is considerably greater than the core material and thus does not affect the basic principle of propagation stated above. The length of the active core region must be sufficient to entertain measurable losses typically about 1" for most liquids.

Although the relationship between the indices of the solid core and the surrounding liquid given by EQ. 1 appears to indicate a specific cutoff in efficient propagation of light when $n_{co} = n_{cl}$ in fact, the change in propagation efficiency as these two quantities approach each other is more gradual as shown in FIG. 1 whereas the response is shown for two core indices as a function of the surrounding liquid index. This graph demonstrates both the gradual decrease in transmission and the requirement to choose the core index to be compatible with the refractive index of the liquid to be measured. This decrease in transmission of the device as a function of surrounding liquid index is the basic principle of operation of this device.

EQ. 1 only indicates the condition for efficient transmission and does not indicate the relative degree of transmission. The actual degree of transmission is determined by the geometry of the active region including its length and diameter. In the case illustrated in FIG. 1, the diameter of the active region is 3 mm and the active length is 25 mm.

The primary object of this invention to provide a refractometer that is suitable for immersion in a liquid to be measured thus overcoming certain limitations associated with existing devices. These limitations include the necessity for entry of the light at certain angles, the necessity for light to travel through the liquid, the necessity to use laser device in single mode operation or to use optical fibers that are subject to deterioration due to corrosive liquids or complex optical components. This invention utilizes the underlying physics of optical waveguide propagation to create a device capable of measuring the refractive index of a liquid via direct immersion of the device in a container containing the liquid.

Because the degree of loss is a function is not only a function of the core and liquid indices but the length of the transmission path as well, the device may use a double pass arrangement to increase its basic sensitivity. This configuration is implemented with conventional optical fibers to input and output light from the device and a reflecting end mirror such that the incident light and reflected light enter and exit from the same end of the device facilitating measurement by immersion.

The device may be calibrated to measure absolute refractive index by referencing the voltage output to the refractive index of known solutions.

The principle embodiment of the device uses a fiber optic assembly to facilitate the entry and exit of the light such that a double pass arrangement through the liquid to be measured can be affected thus facilitating refractive index measurement by immersion of the device.

An alternate embodiment of the device is used to measure the state-of-charge of lead acid batteries by incorporating the device into an enclosure that is mechanically compatible with an existing battery cap.

An alternate embodiment of the device uses an optical window to facilitate the insertion of the fiber optic assembly into the tube surrounding the core.

A further alternate embodiment of the device uses a thermocouple embedded within the fiber optic assembly to facilitate the measurement of the liquid temperature such that the temperature dependence of the refractive index can be corrected.

A further embodiment of the device is the incorporation of the device into a hand-held, battery powered version to facilitate field measurements of liquid refractive index or calibrated in terms of engineering units that are directly related to refractive index such as the specific gravity of sulfuric acid solutions found in lead-acid batteries.

DETAILED DESCRIPTION OF THE INVENTION

Figure 1:
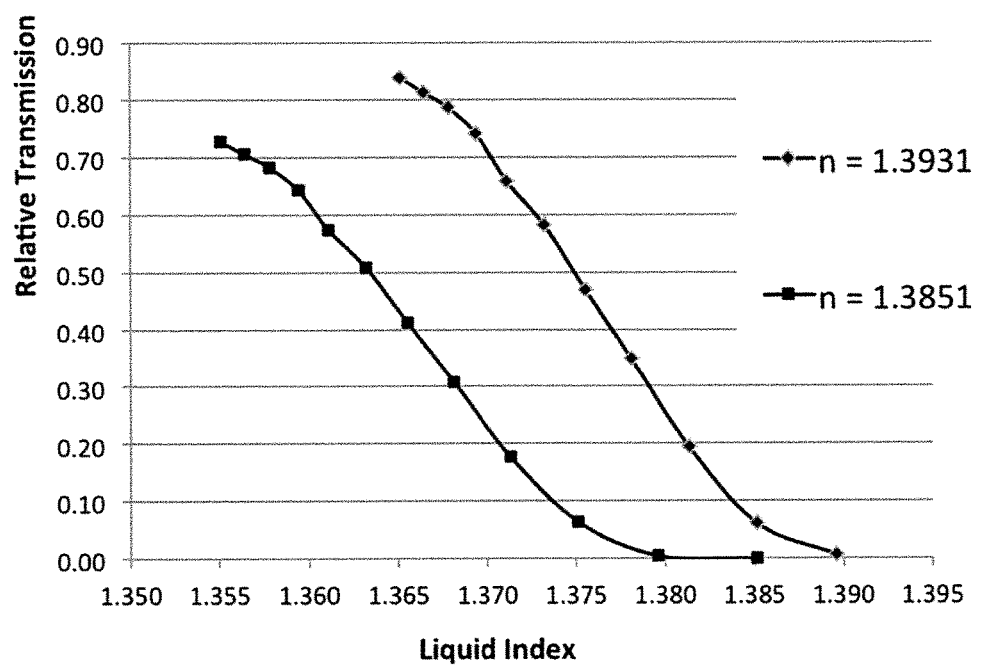
FIG. 1 is a graphical description of the relative change in output signal of the device as a function of the core index and the surrounding liquid index to be measured. It is shown for two different core indices and represents the actual phenomenology on which this invention is based.
Figure 2:
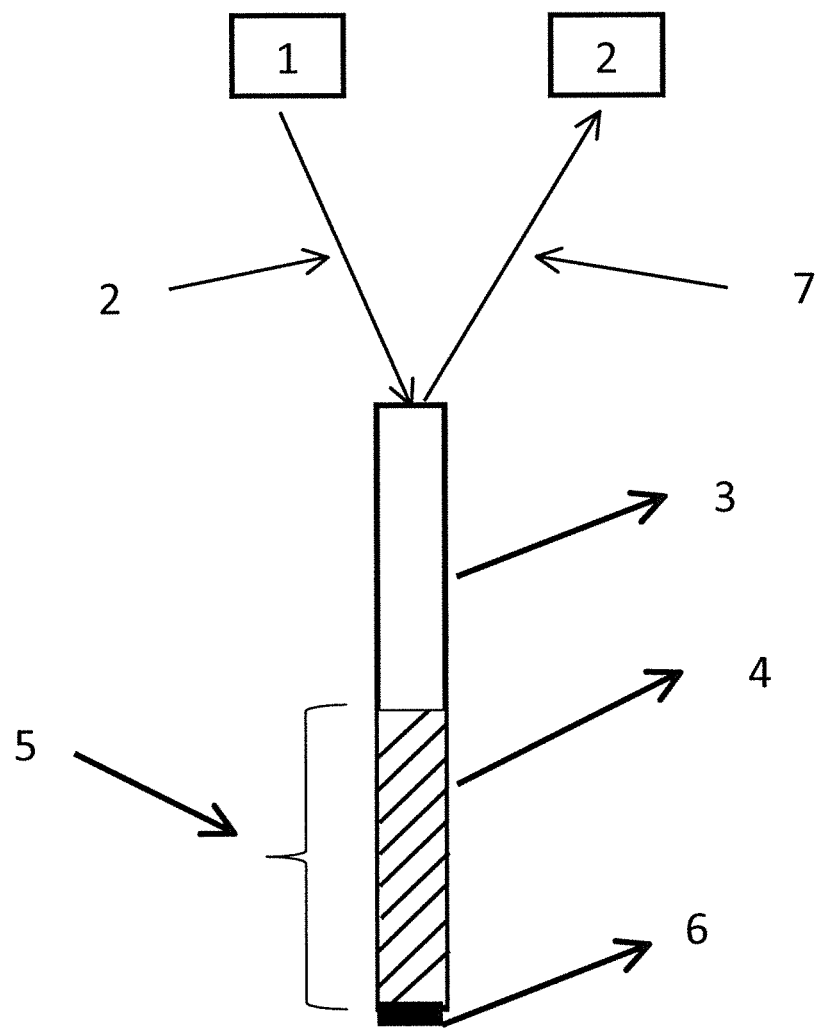
FIG. 2 is a depiction of the major components of the device.

FIG. 1 is a graph of the response of the device as a function of the core index and surrounding liquid refractive index. This graph illustrates a general trend of performance and the requirement to "tune" the refractive index of the core for compatibility of the liquid indices to be measured. This figure represents the phenomenological results on which this invention is based The preferred configuration of the invention for the measurement of the refractive index of a liquid by immersion is shown in FIG. 2. and consists of:
a. Light source 1 such as a LED or laser.
b. A fiber optic means 2 of conveying the light source to the tube surrounding the core
c. A tube 3, impervious and resistant to the surrounding liquid,d whose optical properties do not impact the basic operating principle of the device
d. An active length and diameter 4 of the tube filled with a transparent solid 5 of appropriate index
e. An end-mirror 6 to reflect the light back toward the input increasing the effective length
f. A fiber optic means 7 of conveying the reflected light to a conventional photodetector
g. A photodetector 8 to convert the reflected light to a electrical signal The performance of this device in terms of the signal loss during propagation is a function of tube material, core index, liquid index, tube diameter, tube length, wavelength of the incident light and the numerical aperture of the input source. As the surrounding liquid changes its refractive index the amount of power transmitted through the device changes accordingly thus illustrating the basic principle of operation.

The choice of the tube material is dependent on 3 properties: impervious to the surrounding liquid, the transparency of good quality glass, and of refractive index such that the tube does not impact the basic performance expressed by Eq. 1. This latter property is achieved by choosing a refractive index that is much greater than the core index such as glass, pyrex or preferably quartz with index $\approx 1.54$ at 590 nm. With a tube material index much greater than the core index the conditions for confined rays expressed by Eq. 1 are violated and the tube becomes totally transparent in a waveguide sense relying only on the liquid index to determine the propagation characteristics.

The choice of tube length depends on the tolerable signal loss and the tube diameter. Longer tubes yield more loss because the incident light undergoes more reflections as the light propagates down the tube. The preferred embodiment yields an effective tube length of approximately 2". Length acts in consonance with tube diameter to yield the actual loss as a function of the surrounding liquid index.

The choice of tube diameter is a function of the numerical aperture of the tube input fiber combination. In the configuration above the core region will only propagate light that enters the tube within a certain cone known as the acceptance angle. Eq. 1 can be re-expressed as $$n \sin \theta_{max} = \sqrt{n_{co}^2 - n_{cl}^2} \qquad (2)$$

where n is the refractive index of the entry medium, $n_{co}$ is the refractive index of the core, and $n_{cl}$ is the refractive index of the cladding as before.

Light entering the core at angles greater than $\sin \theta_{max}$ will not undergo total reflection and thus those rays will not be transmitted through the core of the device. In this form, the quantity $n \sin \theta_{max}$ is defined as the numerical aperture (NA) of the system. The number of reflections that a ray undergoes as it traverses the tube is a function of the tube diameter. For a given NA of the entry fibers, larger diameter tubes yield fewer reflections and less loss during propagation.

The number of modes supported by a cylindrical waveguide or optical fiber is proportional to the diameter D of the fiber and given as:

$$N = \frac{\pi D}{\lambda} \sqrt{n_{co}^2 - n_{cl}^2} \qquad (3)$$

where $\lambda$ is the wavelength of light.

The more modes a waveguide is capable of supporting the more power is transported from a multi-mode source.

For a given index of core material, the tube length and diameter work in consonance to yield a certain loss per unit length. There are no reliable analytical predictions of this relationship however in the preferred embodiment of this device with a core material index of 1.38, a tube length of 25 mm and a core diameter of 2 mm yields excellent performance over a liquid index range of 1.36 to 1.38.

Figure 3:
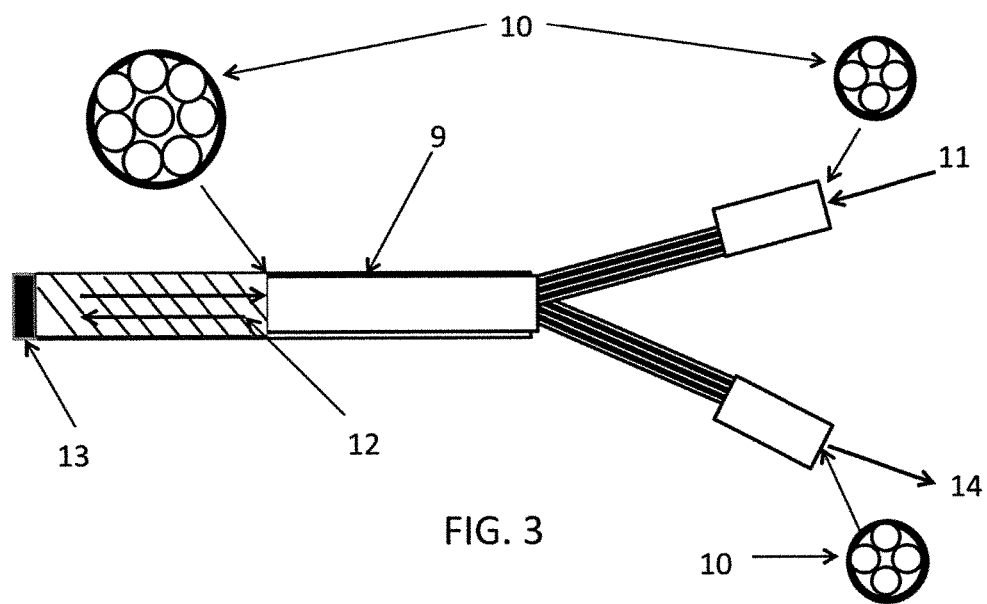
FIG. 3 shows the physical construction of the ferrule assembly containing the fiber optic bundles that input light into the device and output light to the photodetector.

The optical assembly whereby the light may be conveyed in and out of the tube is shown in FIG. 3. The optical assembly consists of a multiplicity of optical fibers encased in a ferrule 9 consisting of independent bundles 10 for both the light input 11 ferrule by way of LED or laser and output light ferrule 14 to a photodetector. The composite ferrule 9 may be of a light absorbing material to minimize anomalous waves travelling between the ferrule body and the tube which may disturb the readings. The input light emerging from the central ferrule 12 is incident normal to the surface of the solid material that comprises the core of the fiber. The principal feature of this assembly is that the light is effectively double passed by means of an end mirror 13 through the active medium thus increasing the effective length and hence the sensitivity of the device.

Figure 4:
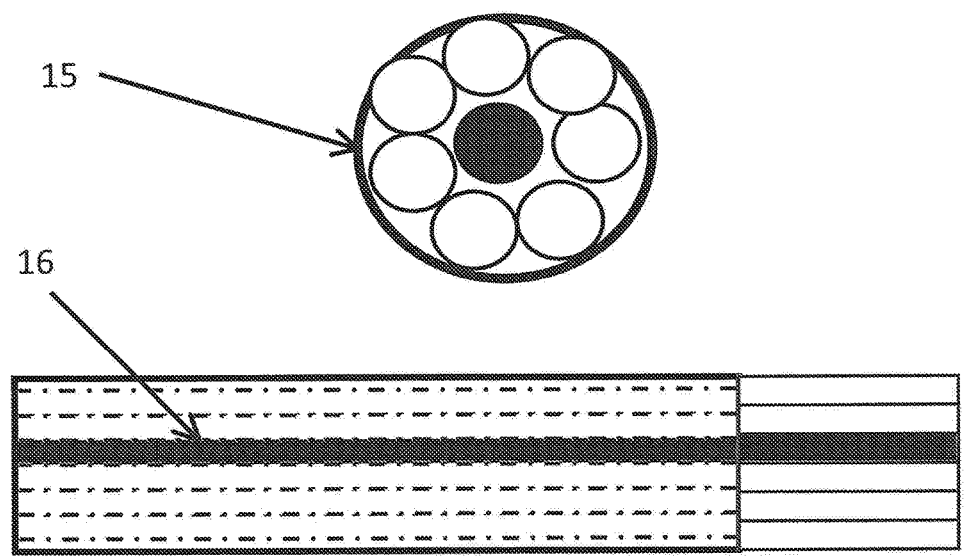
FIG. 4 shows the means by which a small thermocouple, thermistor or RTD may be inserted within the ferrule to measure the temperature of the surrounding liquid.

An alternate configuration of the device shown in FIG. 4 can be used to measure the temperature of the surrounding liquid in addition to the refractive index by inserting a small thermocouple or thermistor, thermocouple or RTD 16 within the fiber bundle 15.

Figure 5:
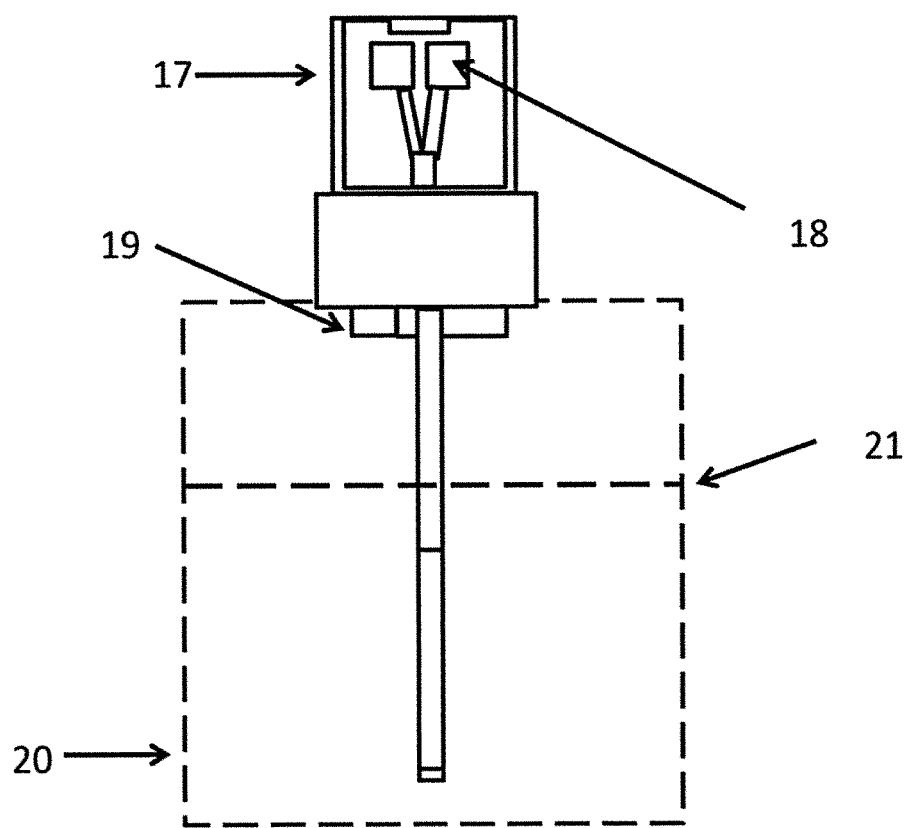
FIG. 5 shows an alternate configuration of the device as implemented in a cell of a typical lead acid battery.

An alternate configuration of the device suitable for insertion into an open port of a conventional lead-acid storage battery cell 20 is shown in FIG. 5. The active region of the tube containing the solid material is immersed in the battery electrolyte 21. The flanged bayonet mounting 19 is designed to be mechanically compatible with the most conventional storage batteries. The cap assembly 17 contains an electronics board 18 containing the light source, photodetector and processing electronics.

Figure 6:
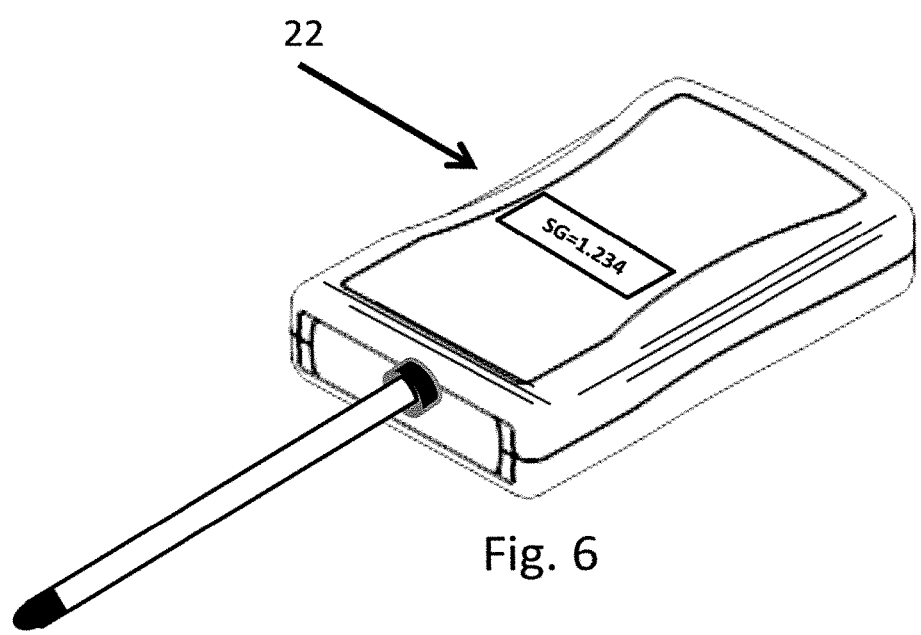
FIG. 6 shows an alternate configuration of the device as implemented in a portable battery powered unit with digital display.

An alternate configuration of the device implemented in a hand-held, battery powered portable device is shown in FIG. 6. This embodiment may be calibrated in terms of suitable engineering units such as specific gravity and displayed 22 using a LCD or LED device.

Figure 7:
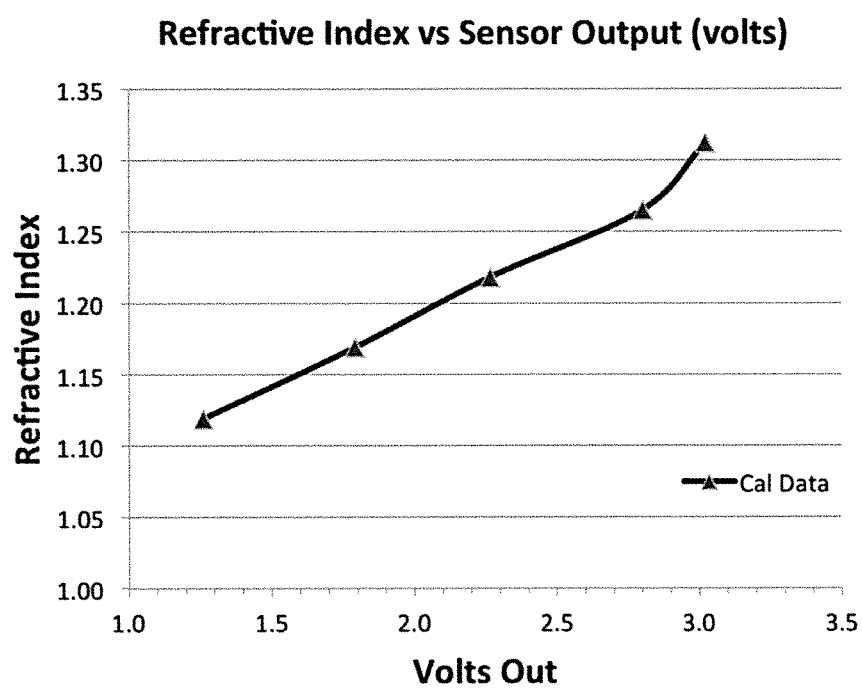
FIG. 7 is a graphical description of the means by which the device may be calibrated in terms of engineering units appropriate to the specific application.

The device may be calibrated as shown in FIG. 7 in terms absolute value of the refractive index or other engineering units related to refractive index by using a series of standard calibration solutions and a curve fitting algorithm such as a polynomial fit to yield accurate values of the units as a function of the output voltage of the photodetector. This technique circumvents such problems as dispersion effects due to the use of differing light source wavelengths.

We claim:

1. A device for quantitatively measuring the refractive index of a liquid comprising:
   (a) a light source configured to produce light with an illumination wavelength;
   (b) an illumination fiber bundle comprising a plurality of optical fibers, said illumination fiber bundle having first and second ends, and mounted with the light source such that light from the light source is communicated to the first end of the illumination fiber bundle;
   (c) a transparent tube having first and second ends, comprising a material that is impervious to the liquid and that has a refractive index that is much greater than the refractive index of the liquid, mounted with the fiber bundle such that light is communicated between the second end of the illumination fiber bundle and the first end of the transparent tube;
   (d) a core material disposed in the core of the transparent tube comprising a material that is transparent to light at the illumination wavelength and has a refractive index approximately equal to or greater than the refractive index of the liquid, disposed within the measuring tube near the second end of the measuring tube;
   (e) a mirror mounted at the second end of the transparent tube such that light propagating through the transparent tube to the second end thereof is reflected by the mirror into the transparent tube toward the first end thereof;
   (f) a detection fiber bundle , having first and second ends, comprising a plurality of optical fibers, mounted with the measuring tube such that light is communicated between the first end of the transparent tube and the first end of the detection fiber bundle;
   (g) a light detector configured to produce a signal responsive to the intensity of light at the illumination wavelength, mounted with the detection fiber bundle such that light is communicated from the second end of the detection fiber bundle to the light detector;
   (h) an analysis system configured to determine the refractive index of the liquid responsive to the signal.

2. The device of claim 1 wherein the refractive index of the core material is equal to or exceeds the upper limit of the refractive index range of the liquid.

3. The device claim 1 wherein the illumination fiber bundle and the detection fiber bundle are bundled together within a ferrule such that light enters and exits at the first end of the transparent tube.

4. The device of claim 1 further comprising a reflecting mirror at the end of the transparent tube positioned orthogonally to the optical axis of the transparent tube such that light traverses the core material twice.

5. The device of claim 1 wherein the illumination fiber bundle is oriented with its long axis parallel to the long axis of the transparent tube axis without regard to specific angle of impingement on the interface between the transparent tube and the core material.

6. The device of claim 1 further comprising an enclosure, wherein elements (a) through (g) of the device mount with the enclosure, and wherein the enclosure is a cap for an open port battery.

7. The device of claim 1 further comprising a temperature sensing element mounted with device such that the temperature sensing element is responsive to a liquid in contact with the portion of the transparent tube containing the measurement material.

8. The device of claim 1 wherein the illumination fiber bundle further comprises a ferrule enclosing the illumination fibers and made of a light absorbing material.

9. The device of claim 1 wherein the light source is configured to produce infrared light with wavelengths >700 nm.

10. The device of claim 1, wherein the light detector signal comprises an electrical signal, and wherein the device further comprises a temperature sensor configured to determine the temperature of the liquid, and wherein the analysis system comprises:
   (j) signal conditioning electronics configured to amplify the electrical signal;
   (k) a model relating intensity of light detected and liquid temperature to refractive index of a liquid surrounding the potion of the measuring tube containing the measurement material.

11. A method of determining the refractive index of a liquid, comprising:
   providing a device as in claim 1;
   placing the transparent tube in the liquid such that the portion of the transparent tube containing the core material is surrounded by the liquid;

using the light source to produce light that travels through the illumination fiber bundle, the transparent tube, the detection fiber bundle, and then to the light detector;

determining the refractive index of the liquid from the signal from the light detector.

12. A method as in claim 11, further comprising using the device to determine the refractive index of a material with a known refractive index surrounding the core material when the device is not in contact with the liquid, and using the refractive index determined to adjust the refractive index determined for the liquid.

13. The device of claim 1, wherein the light source further comprises a focusing lens configured to communicate the light from the light source to the illumination bundle.

14. The device of claim 1, wherein the liquid comprises acid, and wherein the transparent tube is impervious to acid.

* * * * *